United States Patent
Ganti

(10) Patent No.: US 10,550,329 B2
(45) Date of Patent: Feb. 4, 2020

(54) ENERGY EFFICIENT METHOD FOR RECOVERING OIL FROM ASPHALT WASTE UTILIZING BIOREMEDIATION

(71) Applicant: Satyanarayana Ganti, Dover, PA (US)

(72) Inventor: Satyanarayana Ganti, Dover, PA (US)

( * ) Notice: Subject to any disclaimer, the term of this patent is extended or adjusted under 35 U.S.C. 154(b) by 10 days.

(21) Appl. No.: 16/108,210

(22) Filed: Aug. 22, 2018

(65) Prior Publication Data

US 2019/0322943 A1 Oct. 24, 2019

Related U.S. Application Data

(60) Provisional application No. 62/619,258, filed on Jan. 19, 2018.

(51) Int. Cl.
| | |
|---|---|
| *C10C 3/08* | (2006.01) |
| *B01D 12/00* | (2006.01) |
| *C10L 1/02* | (2006.01) |
| *C12P 5/00* | (2006.01) |
| *C08L 95/00* | (2006.01) |

(52) U.S. Cl.
CPC .............. *C10C 3/08* (2013.01); *B01D 12/00* (2013.01); *C10L 1/02* (2013.01); *B01D 2257/702* (2013.01); *C08L 95/00* (2013.01); *C10L 2200/0446* (2013.01); *C10L 2200/0453* (2013.01); *C12P 5/00* (2013.01)

(58) Field of Classification Search
None
See application file for complete search history.

(56) References Cited

U.S. PATENT DOCUMENTS

| | | | |
|---|---|---|---|
| 4,373,961 A | 2/1983 | Stone | |
| 4,640,767 A * | 2/1987 | Zajic | C10G 1/00 |
| | | | 166/246 |
| 4,783,268 A | 11/1988 | Leung | |
| 5,098,025 A | 3/1992 | Drouin et al. | |
| 5,938,130 A | 8/1999 | Zickell | |
| 5,968,349 A * | 10/1999 | Duyvesteyn | C10G 32/00 |
| | | | 208/390 |
| 6,074,558 A * | 6/2000 | Duyvesteyn | C10G 1/045 |
| | | | 208/390 |
| 7,384,181 B1 | 6/2008 | Collette | |
| 7,909,989 B2 | 3/2011 | Duyvesteyn et al. | |
| 8,083,434 B1 | 12/2011 | Gorman et al. | |
| 8,177,152 B2 | 5/2012 | Harmon | |

(Continued)

FOREIGN PATENT DOCUMENTS

CA 2439497 A1 3/2005

OTHER PUBLICATIONS

US Patent and Trademark Office, International Search Report in corresponding PCT/US19/41780, dated Sep. 24, 2019, 7 pages.

*Primary Examiner* — Tam M Nguyen
(74) *Attorney, Agent, or Firm* — Hooker & Habib, P.C.

(57) ABSTRACT

A method for recycling or processing asphalt waste held in a vessel that extracts oil from the waste and cleans the remaining solids includes the steps of adding a reaction solvent into the vessel and into contact with the asphalt waste, adding a bioremediation product into the vessel, adding a quantity of water into the vessel sufficient to effectively stop activity of the bioremediation product, and then removing any oil present in the water from the water. The resulting free oil collected from the process is similar to No. 4 fuel oil.

25 Claims, 2 Drawing Sheets

(56) References Cited

U.S. PATENT DOCUMENTS

| | | |
|---|---|---|
| 8,276,761 B2 | 10/2012 | Kujawa |
| 8,974,661 B2 | 3/2015 | Rennard et al. |
| 2002/0166813 A1* | 11/2002 | Bartlett .................... B09C 1/10 |
| | | 210/610 |
| 2012/0122740 A1* | 5/2012 | Roldan Carrillo ..... C09K 8/582 |
| | | 507/201 |
| 2014/0033951 A1 | 2/2014 | Lafarge |
| 2014/0299018 A1 | 10/2014 | Elseifi et al. |
| 2018/0010305 A1 | 1/2018 | Bentaj et al. |
| 2018/0148744 A1* | 5/2018 | Knight ................. C12N 9/0006 |

\* cited by examiner

ENERGY EFFICIENT METHOD FOR RECOVERING OIL FROM ASPHALT WASTE UTILIZING BIOREMEDIATION

RELATED APPLICATION

This application claims the benefit of and priority to my co-pending U.S. Provisional Patent Application 62/619,258 "Sustainable solution to non-invasive Production of oil from waste asphalt, shingle roof and from oil sands" filed Jan. 19, 2018, said priority provisional application incorporated by reference as if fully set forth herein.

FIELD OF THE DISCLOSURE

The disclosure relates generally to methods for recovering oil from asphalt waste, and in particular to an energy efficient method for recovering oil from asphalt waste bituminous waste utilizing bioremediation that does not require melting the asphalt.

BACKGROUND OF THE DISCLOSURE

Asphalt, also known as bitumen or tar, is a highly viscous liquid or semi-solid form of petroleum. Asphalt is classified by material scientists as a pitch (viscoelastic polymer) that does not have a sharply defined melting point.

Asphalt waste, also referred to as bituminous waste, is a composition that includes asphalt and some other material that is not readily usable "as is". Examples of asphalt waste include (but are not limited to) scrapped or left-over construction products that include asphalt, and tar or oil sands (collectively referred to as "tar sands" herein) that are a combination of bitumen, water, and other solids. Asphalt waste as used herein also encompasses compositions that include instead of asphalt highly viscous, essentially solid (at room temperature) petroleum oils such as heavy fuel oils or intermediate fuel oils that have an asphalt-like consistency at room temperature Asphalt is used in construction products, such as asphalt cement for paving, coatings for sealing and insulation, and in products utilizing asphalt's waterproofing capabilities.

Asphalt is commonly used in the United States in the production of asphalt cement for paving road surfaces. Asphalt cement is made by heating asphalt to an elevated temperature and mixing the heated asphalt with aggregates (stone, sand, gravel, and the like). The asphalt acts as a binder that holds the aggregates together after the heated mixture has cooled. Asphalt concrete typically contains about 5% asphalt by weight.

The roofing industry makes wide use of asphalt to take advantage of asphalt's waterproofing ability. Mastic asphalt is similar to asphalt cement but has a higher asphalt content (typically about 7% by weight). Mastic asphalt is heated and spread on flat roofs to form a waterproof membrane. Asphalt is also used in the manufacture of asphalt roofing shingles. Asphalt is either mixed with a base material or coats a base material to form a waterproof shingle. Recycling asphalt material from shingles and other roofing material is very expensive due to the presence of extraneous material like fiber board, rubber, and other materials.

One of the largest sources of waste asphalt is naturally occurring tar sands found in large parts of North America, particularly in Canada and the United States. Oil can be extracted from tar sands. Standard processes to extract oil from tar sands include surface mining of tar sand deposits and heating tar sand deposits in situ to liquefy the bitumen. Extracting oil from tar sands utilizing these standard processes is complicated and has high environmental and energy costs. This is demonstrated for example, by the process described in Rennard, et al. U.S. Pat. No. 8,974,661.

Recycling asphalt cement is desirable for reusing both the asphalt and aggregates. According to the US Department of Transportation Federal Highway Administration, about 81% of waste asphalt cement is recycled and reused for paving. Recycling waste asphalt shingles is also desirable. Recycled asphalt shingles is a common component used in manufacturing asphalt cement. However, not all types of asphalt shingles can be used in making asphalt cement.

Even with recycling efforts a substantial amount of asphalt waste used for construction and paving end up in landfills. But asphalt waste does not efficiently degrade and therefore consumes much landfill space that becomes unavailable for treating biodegradable wastes.

Asphalt waste may be recycled by heating the waste sufficiently for the asphalt to melt and flow from the remainder of the waste. Often the asphalt waste is heated in a furnace to temperatures exceeding 750 degrees Fahrenheit.

The separation of the asphalt from the remainder of the asphalt waste also enables reuse of the remaining material. But recycling asphalt by melting the asphalt is expensive and energy intensive, requiring large amounts of water and fuel. Burning fuel to heat the asphalt is not a carbon-neutral process and produces large amounts of greenhouse gases. The high cost of recycling works to limit recycling of many types of asphalt waste.

Thus there is a need for an energy efficient method for recycling or processing asphalt waste that does not require melting the asphalt, and can be used for recycling or processing many different types of asphalt waste.

SUMMARY OF THE DISCLOSURE

Disclosed is a method for recycling or processing asphalt waste that does not require melting the asphalt. The disclosed method can be used with many different types of asphalt waste, including (but not limited to) asphalt cement, asphalt shingles, and tar sands. Additional benefits of the disclosed process are that it utilizes inexpensive ingredients that are environmentally friendly, and that water used in the process can be easily recycled and reused in the process.

The disclosed method for recycling or processing asphalt waste is unique in that it utilizes bioremediation products that breakdown the complex hydrocarbons present in the asphalt of asphalt waste. A bioremediation product typically includes a consortium of bacteria/microorganisms that remediate petroleum oils released in water, soil, or even present in the form of fumes or odors. Such microorganisms include (but are not limited to) hydrocarbonoclastic microorganisms. Hydrocarbonoclastic microorganisms degrade or "biofractionate" hydrocarbons by utilizing hydrocarbon oils as a food source, "eating" and thereby breaking the hydrocarbon molecules.

Hydrocarbonoclastic bacteria (HCB) are an important class of hydrocarbonoclastic microorganisms. Examples of HCB are disclosed in my U.S. Pat. No. 6,267,888 "Biodispersion as a Method For Removal of Hydrocarbon Oil From Marine Aquatic Environments", which patent is fully incorporated by reference herein. In general, the species or strains of hydrocarbonoclastic bacteria may be derived from *Pseudomonas, Phenylobacterium, Stenotrophomonas, Gluconobacter, Agrobacterium, Vibrio, Acinetobacter*, or *Micrococcus*. Exemplary bacterial strains include *Pseudomonas pseudoalkaligenes, Phenylobacterium immo-* bile, *Stenotrophomonas maltophilia, Gluconobacter cerinus*, or *Agrobacterium radiobacter*. Hydrocaronoclastic bacteria may also be widely derived from genera belonging to *Pseudomonas, Phenylobacterium, Stenotrophomonas, Gluconobacter, Agrobacterium, Vibrio, Acinetobacter,* or *Micrococcus*. Exemplary species include *Pseudomonas pseudoalkaligenes, Phenylobacterium immobile, Stenotrophomonas maltophilia, Gluconobacter cerinus, Agrobacterium radiobacter* or *Pseudomonas alkaligenes*. Bioremediation products may include hydrocarbonoclastic bacteria which have been genetically manipulated or otherwise bioengineered and may include yeasts.

X A non-limiting example of a commercially available bioremediation product that can be used in the disclosed method is the VAPORREMED® brand bioremediation product available from Sarva Bio Remed, LLC 25 Marianne Drive, York, Pa. 17406. The VAPORREMED bioremediation product is a 5% suspension of vegetable oil with water containing a consortium of oil degrading bacteria. The VAPORREMED bioremediation product has been found in many applications to eliminate fuel oil fumes or odors almost instantly.

As used herein a reaction solvent is a solvent that is capable of initiating a reaction that at least partially dissolves asphalt at room temperature. Examples of reaction solvents include (but are not necessarily limited to) diesel fuel, kerosene, aviation fuel, gasoline, chloroform, carbon disulfide, and organic solvents such as xylene, toluene, and benzene.

In preferred embodiments of the disclosed method diesel fuel is used as the reaction solvent. Reaction solvents having a low boiling point or release chlorine or sulfur are generally not preferred reaction solvents for use in the disclosed method and thus gasoline, chloroform, and carbon disulfide are not preferred reaction solvents.

The asphalt waste to be recycled is placed in a vessel. In embodiments of the disclosed method, the method includes the steps of:

(a) adding a reaction solvent into the vessel and thereby having the reaction solvent coming into contact with the asphalt waste in the vessel;

(b) adding a bioremediation product into the vessel whereby the asphalt waste comes into contact with the bioremediation product;

(c) After performing steps (a) and (b), adding a quantity of water into the vessel sufficient to effectively stop activity of the bioremediation product and enabling oil liberated from the asphalt waste to separate from the asphalt waste, and (d) removing the water from the reactor vessel and removing any oil present in the water from the water.

The oil referred to in step (d) and recovered from the water is released from the asphalt waste. Analysis of a sample of the recovered oil demonstrates properties similar to Number 4 fuel oil. The flash point of the oil sample was 76 degrees Centigrade, the viscosity at 40 degrees Centigrade was 7.18 Centistokes and total sulfur was 1,828 parts per million.

It is theorized (and such theory is not intended to be limiting and is based on observing the disclosed method acting on asphalt waste) that the reaction solvent in contacting the asphalt waste draws out asphalt from the waste, and that the microorganisms in the bioremediation product further assist in drawing out the asphalt and accelerating the release of oil, transforming the asphalt into an oil-like form that is carried away with the water.

Addition of the bioremediation product following the addition of the reaction solvent substantially arrests the activity of the reaction solvent and—substantially reduces the hazard potential of the reaction solvent.

Preferably step (a) is performed before step (b), that is, the reaction solvent is added to the vessel before adding the bioremediation product. This enables the reaction solvent to initiate dissolving the asphalt without being diluted by the addition of the bioremediation product. Adding the bioremediation product after the reaction solvent also enables the bioremediation product to mitigate any fumes generated by the reaction solvent and aids in remediating the reaction solvent.

If step (b) is performed before step (a), that is, the bioremediation product is added to the vessel before the reaction solvent, it is preferred that an additional amount of the bioremediation product be added to the vessel after adding the reaction solvent. It has been observed in testing that adding the bioremediation product to the vessel before adding the reaction solvent results in lower oil yields. Adding the additional bioremediation product after adding the reaction solvent improves the oil yield.

Preferably the bioremediation product or the additional bioremediation product is added to the vessel about 30 seconds to 2 minutes after the reaction solvent is added to the vessel. It is believed this enables the reaction solvent to initially maximize contact with the asphalt waste and initiate dissolving of the asphalt over a maximum area of the asphalt waste before being remediated by the bioremediation product.

Step (c) is preferably performed about 2 minutes to 5 minutes after steps (a) and (b). That is, the water is added to the vessel after the reaction solvent and bioremediation product have had some time to be active with the asphalt waste. The microorganisms in the bioremediation product may even consume the oil being produced from the asphalt waste. The bioremediation product is given some time to work with the reaction solvent to produce the oil, but not enough time to substantially affect the productivity of the process. Enough water is added to the vessel to sufficiently dilute the bioremediation product and thereby effectively stop the activity of the bioremediation product in the vessel.

The water added to the vessel is preferably without contaminants that would adversely pollute the oil generated from the process. Because the water is added to halt the activity of the microorganisms in the bioremediation product, steps (a)-(d) may be repeated a number of times with an initial starting amount of waste asphalt to capture as much oil as possible. Typically steps (a)-(d) are repeated 5 to 10 times before the amount of oil being recovered falls to amounts too small to economically separate from the water (and the waste looks clean).

Typically the material remaining in the vessel after recovering the oil is clean enough for recycling and reuse. The asphalt has been removed and the remaining material is essentially asphalt-free. If there are hydrocarbons on the remaining material, the material can be removed from the vessel and treated with a bioremediation product (which may be the same as the bioremediation product) as a final cleaning step.

The disclosed method for recycling asphalt waste has a number of advantages.

The method can be conducted at room temperature and can use tap water also at room temperature. Thus the process has an essentially zero carbon footprint.

The water used in the process can be recycled and reused, making the process ecologically sustainable and environmentally friendly.

There is no need to heat the asphalt waste or expose the asphalt waste to steam or other high-temperature agents. The disclosed method is relatively fast, even when repeating method steps. It is not unusual when recycling asphalt cement for example to begin the method at the start of the work day, collect the oil, and have remaining clean aggregate before the end of the day.

Inexpensive materials are used, and the vessel can be mounted on a trailer for easy transport to recycling sites or cleanup sites. For example, the disclosed method may be used at a fuel spill to remove heavy fuel oil that has spilled onto beach sand Other objects and features of the disclosure will become apparent as the description proceeds, especially when taken in conjunction with the accompanying drawing sheets.

DETAILED DESCRIPTION

Figure 1:
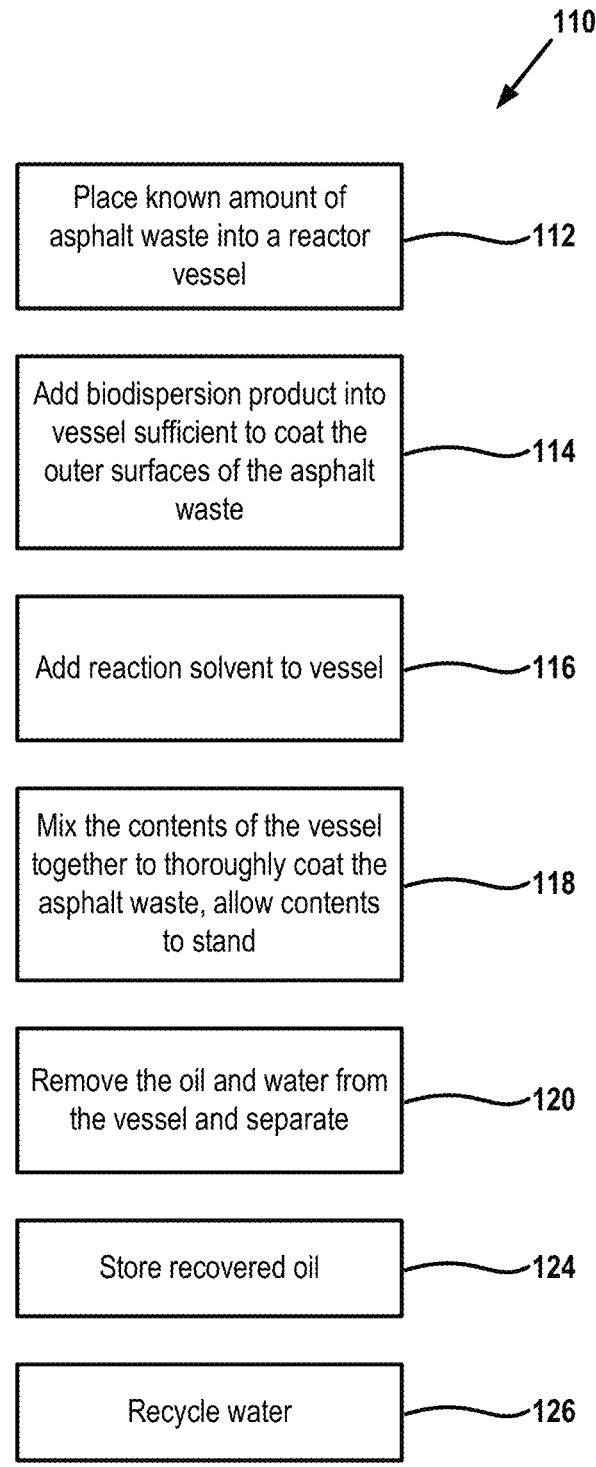
FIG. 1 is a flow chart illustrating the steps of the disclosed method.

FIG. 1 illustrates the steps of an embodiment 110 of the disclosed method for recycling asphalt waste. The method embodiment 110 is being conducted in an indoor work environment having a room temperature of 75 degrees Fahrenheit.

The asphalt waste had been previously crushed and pulverized to increase the surface area to volume ration of the waste. Crushing and pulverizing the asphalt waste is optional but can reduce the number of times the process must be repeated to recover the oil.

In the initial step 112, an amount of the asphalt waste is placed in a reaction vessel. When gaining experience with the process, it is helpful to use a known amount of asphalt waste and record the amount of the reaction solvent, bioremediation product, and water are used to aid in optimizing the amounts used.

In this embodiment a bioremediation product is then added to the vessel in the step 114. The bioremediation product may be the VAPORREMED bioremediation product described previously above. An advantage of the VAPORREMED bioremediation product is that it helps suppress oil fumes that may be generated in carrying out the process. The bioremediation product may be sprayed onto the asphalt waste or poured into the vessel, depending on how the microorganisms in the bioremediation product are packaged.

Sufficient bioremediation product is added to coat all the outer surfaces of the asphalt waste.

A reaction solvent is then added in the step 116. The reaction solvent may be diesel fuel.

The reaction solvent, bioremediation product and the asphalt waste in the vessel are then mixed together for less than one minute to wet the entire outer surfaces of the asphalt waste in step 118. After mixing the vessel contents are allowed to stand for 2 minutes so that the reaction solvent and bioremediation product can be active and generate free oil from the asphalt waste.

In the next step 120 clean fresh water is added to the vessel. The water may be tap water, or filtered water free of particulates obtained from some other water source. The amount of added water is sufficient to entirely cover the asphalt waste and sufficiently dilute the bioremediation product in the vessel so that the activity of the microorganisms in the vessel effectively ends. The contents of the vessel can be allowed to stand for a few minutes to enable oil to float free of the asphalt waste.

In the next step 122 the oil and water is then removed from the vessel, sent to an oil-water separator, and the oil is separated from the water utilizing the oil-water separator in the next step 120. An oil/water separator suitable for use in the disclosed method is the ECOLINE-A™ oil-water separator with an automatic oil draw-off device available from Freytech, Inc., Miami, Fla., USA.

The oil separated from the water is stored in a storage vessel in the next step 124. The water with the oil removed is collected for method reuse in the step 126. The collected water can be recycled for some other use if desired.

Steps 114-126 can be repeated as many times as needed until essentially no fresh oil is being generated, the asphalt waste is essentially free of asphalt, and the remaining solids are free of asphalt.

Figure 2:
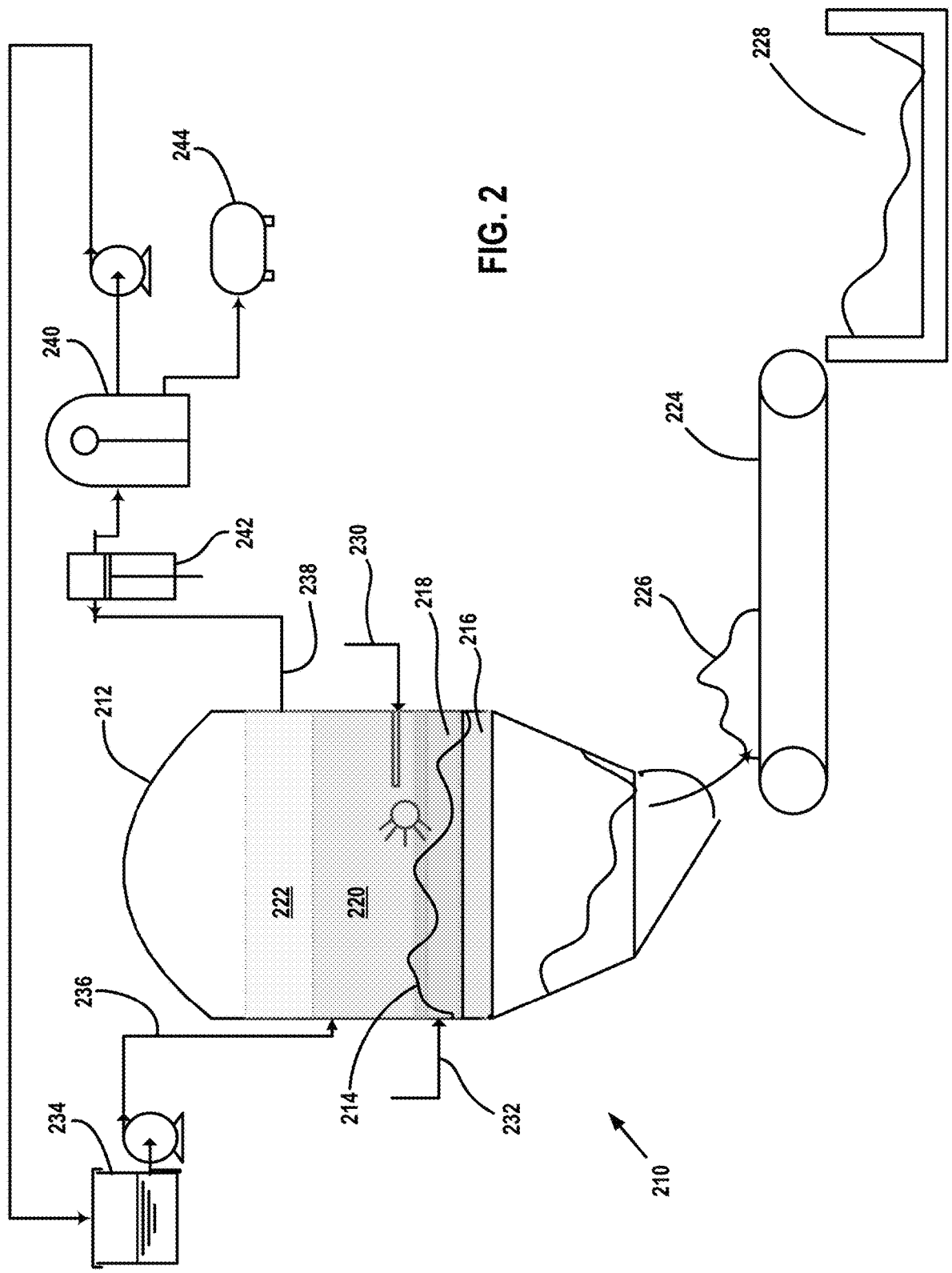
FIG. 2 is a schematic diagram of a mechanical system or apparatus for carrying out the disclosed method.

FIG. 2 illustrates a system or device 210 for performing the disclosed cold process for production of oil from asphalt waste.

The device 210 includes a process tank 212 that receives the asphalt waste 214, the reaction solvent indicated as a fluid layer 216, the bioremediation product indicated as a layer 218, and the water indicated as a layer 220. Free oil generated during the process floats on the water and is indicated as an oil layer 222. The bottom of the tank empties onto a conveyor 224 that transports the solids 226 remaining after the process is completed away from the process tank. In the illustrated embodiment the conveyor conveys the solids to a bioremediation pit 228 for optional additional post-process bioremediation treatment to remove any remaining asphalt or oil wastes from the solids.

A reaction solvent line 230 flows the reaction solvent from a source of reaction solvent (not shown) into the process tank 212. A bioremediation product line 232 flows the bioremediation product from a source of bioremediation product (not shown) into the process tank.

A water tank 234 provides the fresh water needed for carrying out the process. The water tank is connected to a water supply line 236 that discharges water from the water tank into the process tank 212. A water discharge line 238 flows the oil/water mixture out of the process tank and to an oil/water separator 240 via the water pump 242. The oil discharged from the separator is stored in the storage tank 244. The water discharged from the separator is returned to the water tank 234 for reuse.

Three non-limiting illustrative applications of the disclosed method to different types of asphalt waste are described below.

Example 1 Waste Asphalt Cement. A sample of waste asphalt cement was collected from a parking lot and broken into small pieces. A one-hundred gram sample of the pulverized asphalt waste was placed in each of a number of glass beakers.

Ten milliliters (10 mL) of diesel fuel was added to each beaker, soaking of the asphalt waste in the beaker. Forty milliliters (40 mL) of the VAPORREMED bioremediation product was then added to each beaker about 30 seconds after adding the diesel fuel. After about 2 minutes, fresh water was added to each beaker that completely immersed the asphalt waste. Very shortly thereafter a layer of oil was visible to the naked eye floating on the top surface of the water in each beaker. The water was removed from each beaker without disturbing the asphalt waste in the beaker. Some of the oil in each beaker remained behind, coating the sides of the beaker. The beakers were rinsed with additional diesel fuel and water to help remove the oil adhering on the beaker walls.

The process of adding diesel fuel, the VAPORREMED bioremediation product, and then fresh water was repeated for a total time of about 2 to 4 hours until no more oil was being collected. The remaining aggregate in the beakers was clean, asphalt-free, and was in condition for recycling. If there had been oil adhering to the remaining aggregate, a bioremediation product could have been applied to the aggregate to remove the oil as a final step in the process.

As a result of the process, each beaker of 100 grams of waste asphalt cement generated on average 250 milliliters (250 mL) of oil. An oil sample was tested and found to be similar to No. 4 fuel oil as previously described.

Frequent solvent rinsing of the beakers to dissolve the adhering oil helped increase oil productivity.

By contrast, immersing 100 grams of the waste asphalt cement in diesel fuel dissolved the asphalt in about 24 hours but without recovery of oil.

Example 2: Asphalt Shingle Waste. A new asphalt shingle was purchased from a local retainer. The asphalt layer was scraped into a vessel and essentially the same process described above was repeated with the asphalt shingle waste.

The free oil that was collected was similar in appearance and quality to the oil collected from the asphalt cement waste.

Example 3: Tar Sands. A sample of tar sands from the Athabasca region of Canada was obtained. The sample was uniformly broken into small pieces and placed at the bottom of a vessel. Essentially the same process as described above for the asphalt cement waste and the asphalt shingle waste was repeated with the tar sands sample.

After repeating the reaction solvent—bioremediation product—water rinse steps five times to collect the free oil released from the tar sands, the sand remaining in the vessel appeared clean to the naked eye. The sand was removed from the vessel and the sand was exposed to a bioremediation product so that any oil possibly remaining in the sand was removed. The sand was now clean and suitable for recycling.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art, as well as such changes and alterations that fall within the purview of the following claims.

What is claimed is:

1. An environmentally friendly, low carbon footprint method for recycling or processing an amount of asphalt waste being held in a vessel, the method comprising the steps of:
   (a) adding a reaction solvent into the vessel and thereby into contact with the asphalt waste in the vessel;
   (b) adding a bioremediation product into the vessel whereby the asphalt waste comes into contact with the bioremediation product;
   (c) after performing steps (a) and (b), adding a quantity of water into the vessel sufficient to effectively stop activity of the bioremediation product; and
   (d) removing the water from the reactor vessel and removing any oil present in the water.

2. The method for recycling or processing asphalt waste of claim 1 including the step of repeating steps (a) through (d) multiple times before emptying the vessel.

3. The method for recycling or processing asphalt waste of claim 2 wherein the step of repeating steps (a) through (d) is terminated after the quantity of oil separated from the water in step (d) falls below a predetermined value.

4. The method for recycling asphalt waste of claim 1 wherein the liquid reaction solvent is diesel fuel.

5. The method for recycling or processing asphalt waste of claim 1 wherein the liquid bioremediation product comprises a mixture of vegetable oil, water and live microorganisms.

6. The method for recycling or processing asphalt waste of claim 5 wherein the live microorganisms comprise hydrocarbonoclastic microorganism.

7. The method for recycling or processing asphalt waste of claim 1 wherein step (a) further comprises the step of simultaneously agitating the reaction solvent in the vessel and the asphalt waste.

8. The method for recycling or processing asphalt waste of claim 7 wherein the step of agitating comprises physically mixing together the reaction solvent and the asphalt waste.

9. The method for recycling or processing asphalt waste of claim 1 wherein the water removed from the vessel in step (d) is recycled and reused for performing step (c) with the same waste asphalt or a different amount of waste asphalt.

10. The method for recycling or processing asphalt waste of claim 1 wherein the asphalt waste comprises one or more of: asphalt cement, asphalt shingles, and tar sand.

11. The method for recycling or processing asphalt waste of claim 1 wherein the asphalt waste comprises aggregates, the method further comprising the step of:
   (e) removing the aggregates from the vessel after performing the steps (a)-(d) one or more times, the aggregates when removed from the vessel being sufficiently free of asphalt to be used as clean fill.

12. The method for recycling or processing asphalt waste of claim 1 wherein the asphalt waste comprises aggregates, the method further comprising the step of:
   (e) removing the aggregates from the vessel after performing the steps (a)-(d) one or more times, and
   (f) further remediating the removed aggregate utilizing a bioremediation product.

13. The method for recycling or processing asphalt waste of claim 1 wherein the asphalt waste in the vessel comprises asphalt, and the asphalt waste is not exposed to temperatures above the melting point of the asphalt when carrying out steps (a)-(d).

14. The method for recycling or processing asphalt waste of claim 13 wherein the asphalt waste is exposed to temperatures only below the boiling point of water when carrying out steps (a)-(d).

15. The method for recycling or processing asphalt waste of claim 14 wherein the asphalt waste is exposed to temperatures at or below 80 degrees Fahrenheit.

16. The method for recycling or processing asphalt waste of claim 13 wherein the asphalt waste is at an initial temperature when placed in the vessel, the asphalt waste not being exposed to temperatures that substantially increases the softness of the asphalt waste when carrying out steps (a)-(d).

17. The method for recycling or processing asphalt waste of claim 1 wherein step (a) is performed before step (b).

18. The method for recycling or processing asphalt waste of claim 17 wherein step (b) is performed between 30 seconds and 5 minutes after step (a).

19. The method for recycling or processing asphalt waste of claim 1 wherein step (c) is performed between 2 minutes and 5 minutes inclusive after performing steps (a) and (b).

20. The method for recycling or processing asphalt waste of claim 1 wherein step (b) is performed before step (a), and step (a) includes the step of adding an additional amount of a bioremediation product into the vessel after adding the solvent.

21. The method for recycling or processing asphalt waste of claim 1 wherein the steps are conducted in a room-temperature environment.

22. The method for recycling or processing asphalt waste of claim 1 wherein the asphalt waste comprises heavy fuel oil or intermediate fuel oil.

23. The method for recycling or processing asphalt waste of claim 1 wherein the oil removed from the water in step (d) is similar to #4 fuel oil.

24. A method for recycling or processing asphalt waste comprising the steps of:

(a) bringing an amount of asphalt waste into contact with a reaction solvent;

(b) bringing the asphalt waste into contact with a bioremediation product and thereby initiating bioremediation activity by the bioremediation product on petroleum components of the asphalt waste;

(c) after performing steps (a) and (b), bringing the asphalt waste into contact with a sufficient amount of water to dilute the bioremediation product and thereby effectively stop activity of the bioremediation product; and (d) removing any oil present in the water after performing step (c).

25. The method for recycling or processing asphalt waste of claim 24 wherein the bioremediation product comprises a suspension of vegetable oil and water, the suspension containing oil degrading bacteria.

* * * * *